(12) United States Patent
Evans et al.

(10) Patent No.: US 6,214,824 B1
(45) Date of Patent: Apr. 10, 2001

(54) USE OF AMILORIDE FOR TREATING CANCER

(75) Inventors: Douglas McCullough Evans; Kimberly Denise Sloan-Stakleff, both of Akron, OH (US)

(73) Assignees: Douglas M. Evans; Kimberly D. Sloan-Stakleff, both of Akron, OH (US)

( * ) Notice: Subject to any disclaimer, the term of this patent is extended or adjusted under 35 U.S.C. 154(b) by 0 days.

(21) Appl. No.: 09/370,643

(22) Filed: Aug. 6, 1999

Related U.S. Application Data

(63) Continuation-in-part of application No. 09/154,345, filed on Sep. 16, 1998, now abandoned.

(51) Int. Cl.$^7$ ............... A61K 31/54; A61K 31/495
(52) U.S. Cl. ................... 514/224.2; 514/255.06
(58) Field of Search ............... 514/224.2, 255.06

(56) References Cited

PUBLICATIONS

Pashinskii, Byull. Eksp. Biol. Med., 74(11), 82–4 Abstract Only, 1972.*
Pashinskii, Farmakol. Toksikol., 36(5), 602–5 Abstract Only, 1973.*
Tatsuta et al., Carcinogenesis, 16(4), 941–2 Abstract Only, 1995.*

* cited by examiner

Primary Examiner—Jerome D. Goldberg
(74) Attorney, Agent, or Firm—Frederick K. Lacher; Marcella R. Lacher

(57) ABSTRACT

Use of the proprietary drug amiloride for the treatment of cancer types that depend on an enzymatic cascade triggered by the activation of plasminogen to plasmin by the specific activating enzyme Urokinase Plasminogen Activator (uPA). Administration of amiloride inhibits the action of uPA, inhibits the ability of the cancer cell to attract new blood supply, blocks the Na+/H+ transporter, and inhibits ornithine decarboxylase necessary for DNA synthesis. Further, in combination with amiloride, a different step in the enzymatic cascade is targeted by a secondary agent, Batimistat, for example, which is a metalloprotease inhibitor. Additionally, the use of hydrochlorothiazide promotes excretion of potassium.

4 Claims, 4 Drawing Sheets

USE OF AMILORIDE FOR TREATING CANCER

This application in a continuation-in-part application of application Ser. No. 09/154,345 filed Sep. 16, 1998, now abandoned.

BACKGROUND OF THE INVENTION

1. Field of Invention

This invention pertains to the art of methods for suppressing the invasion and spread of cancer cells and more particularly to the use of amiloride, alone or in combination with other agents, to inhibit the proliferation and invasive capability of epithelial based cancers which are dependent on the plasmin enzymatic cascade.

2. Background of the Invention

Cancer cells proliferate through a series of events such as separation of cells from the primary tumor mass, migration of the separated cells through solid tissue, penetration of the vascular system with embolization at a distant site (intravasation), escape of embolic cells from the confines of the capillary bed involved (extravasation), and parasitization of blood supply at the target site.

The mechanisms which allow these events to occur are perversions of normal physiologic processes and are dependent on a cascade of enzymatic activity which is initiated by the intracellular chemistry of the cancer cell. The trigger for this cascade is the activation of plasminogen to plasmin. This activation is a physiologic function which normally allows for the dissolution of blood clots within the vascular system, allows for the migration of blood cells through solid tissue to fight infection or to reject foreign material, and allows for the penetration of the ovum by the sperm cell.

In the cancer cell, large amounts of plasminogen activator, uPA, are produced. This activator binds to its own cell surface receptor sites. The surface-bound activator captures plasminogen from the circulatory system and converts it to the active form of plasmin. In turn, plasmin lyses the basement matrix, allowing the liberated cell to migrate through solid tissue. Plasmin also activates other tissue enzymes which dissolve connective tissue and the binding molecules of the cell wall of capillaries.

The end result of this complex activity is the local invasion of specific cancer cells as well as the capacity of those cells to invade the circulatory system and spread to distant sites. The types of cancer cells so affected are those derived from epithelial cells. These cancer types include the most commonly found in man, such as breast, colon, stomach and lung.

One trigger mechanism for the enzymatic cascade is the activation of plasminogen to plasmin by the specific activating enzyme Urokinase Plasminogen Activator or uPA. The capacity of the cancer cell to invade and spread may be depressed by inhibition of this trigger mechanism.

One substance which has been found to inhibit the activator, uPA, is a acylguanidine, known under the proprietary name, Amiloride. This drug is a potassium sparing diuretic which has been marketed for years for the purpose of controlling hypertension. It is used most often in conjunction with more powerful diuretics. Amiloride prevents the loss of potassium which occurs with those diuretic agents.

In 1988, an article by J. A. Kellen et. al. (Antimetastatic Effect of Amiloride in an Animal Tumor Model, Anticancer Res, 8, 1373–1376) presents a study using Fisher rats inoculated with breast cancer cells. The in vivo study showed that continuous administration of Amiloride via drinking water prevented the formation of lung cancer in the study animals.

The present invention confirms the suppression of experimentally induced metastases through the use of amiloride. In addition, a time and dose-dependency relationship of amiloride administration is demonstrated in the present invention.

Because known inhibitors in the art will suppress, but not eliminate the invasive capability of the cancer cells, one may surmise that more than the above-mentioned trigger mechanism in the enzymatic cascade should be targeted. A combination of inhibitors which attack separate parts of the chain reaction forms a part of the present invention.

In addition to the use of amiloride alone, the present invention is directed to the combination of the action of amiloride, which is a uPA inhibitor, with a metalloprotease inhibitor such as Batimistat which is a proprietary name of British Biotech, and/or hydrochlorothiazide, which promotes the excretion of potassium which could be retained by the other inhibitors.

SUMMARY OF THE INVENTION

Amiloride has been found to exhibit other remarkable pharmacological effects as well as inhibiting uPA. Amiloride inhibits the ability of the cancer cell to attract new blood supply. It blocks the Na+/H+ transporter, the required mechanism for cell multiplication, and inhibits still another enzyme, ornithine decarboxylase which controls DNA synthesis. Therefore, it has been found that amiloride inhibits the spread of cancer cells in at least four separate and distinct ways.

In accordance with the present invention, there is provided a method for treating cancer comprising the step of administering to a host an effective amount of amiloride.

In accordance with one aspect of the invention, the amiloride is administered to a host that has a cancer from epithelial cells including breast cancer, colon cancer, stomach cancer, and lung cancer.

According to another aspect of the invention, there is provided a method for treating diseases in which cell proliferation is a primary or secondary cause comprising the step of administering to a host in need of treatment an effective amount of amiloride.

According to another aspect of the invention, there is provided a method for suppressing an invasive capacity of cancer cells comprising the step of administering to a host an effective amount of amiloride.

According to another aspect of the invention, there is provided a method for treating a host having cancer cells derived from epithelial cells due to an enzymatic cascade triggered by the activation of plasminogen to plasmin by the specific activation of Urokinase Plasminogen Activator (uPA) comprising the step of administering to the host an amount of amiloride sufficient to adversely affect the action of the uPA and thereby suppress evasion and spread of cancer cells in the host.

According to another aspect of the invention, the method further comprises the step of administering a secondary agent to the host in combination with the amiloride.

According to another aspect of the invention, the secondary agent is effective to suppress a different step in the enzymatic cascade than the action of the uPA.

According to another aspect of the invention, the secondary agent is batimistat.

According to another aspect of the invention, the secondary agent promotes the excretion of potassium.

One advantage of the invention is that amiloride is a drug which has already been shown to be tolerated by humans in the treatment of other conditions.

Another advantage of the invention is that amiloride is readily available.

Another advantage of the invention is that amiloride does not depend on a toxic effect on human cells in order to be effective.

Another advantage of the invention is that use of secondary agents increases the benefit to the host as compared to the use of amiloride alone.

Another advantage of the invention is the suppression of the migratory capability of cancer cells.

Still other benefits and advantages of the invention will become apparent to those skilled in the art to which it pertains upon a reading and understanding of the following detailed specification.

DESCRIPTION OF THE PREFERRED EMBODIMENT

The invention is used in connection with treating a cancer in a host, particularly those types of cancers which are derived from epithelial cells such as breast cancer, colon cancer, stomach cancer, lung cancer, etc.

Of particular concern is the invasion and spread of cancer cells which is the primary mechanism of death from such diseases. It has been shown that the activation of plasminogen to plasmin by the specific activating enzyme Urokinase Plasminogen Activator (uPA) begins a process which allows cancerous cells to not only invade local sites, but also to enter the circulatory system and migrate to distant sites. Inhibition of uPA therefore suppresses the ability of the cancer cell to invade and spread.

Applicants have initiated several studies of amiloride usage for the suppression of breast cancer in rats. Further, Applicants have compared amiloride to a synthetic inhibitor of uPA, and did a study of the effects of amiloride on three separate cell lines of human breast cancer. The results of these efforts are set forth in FIGS. 1–4.

Figure 1:
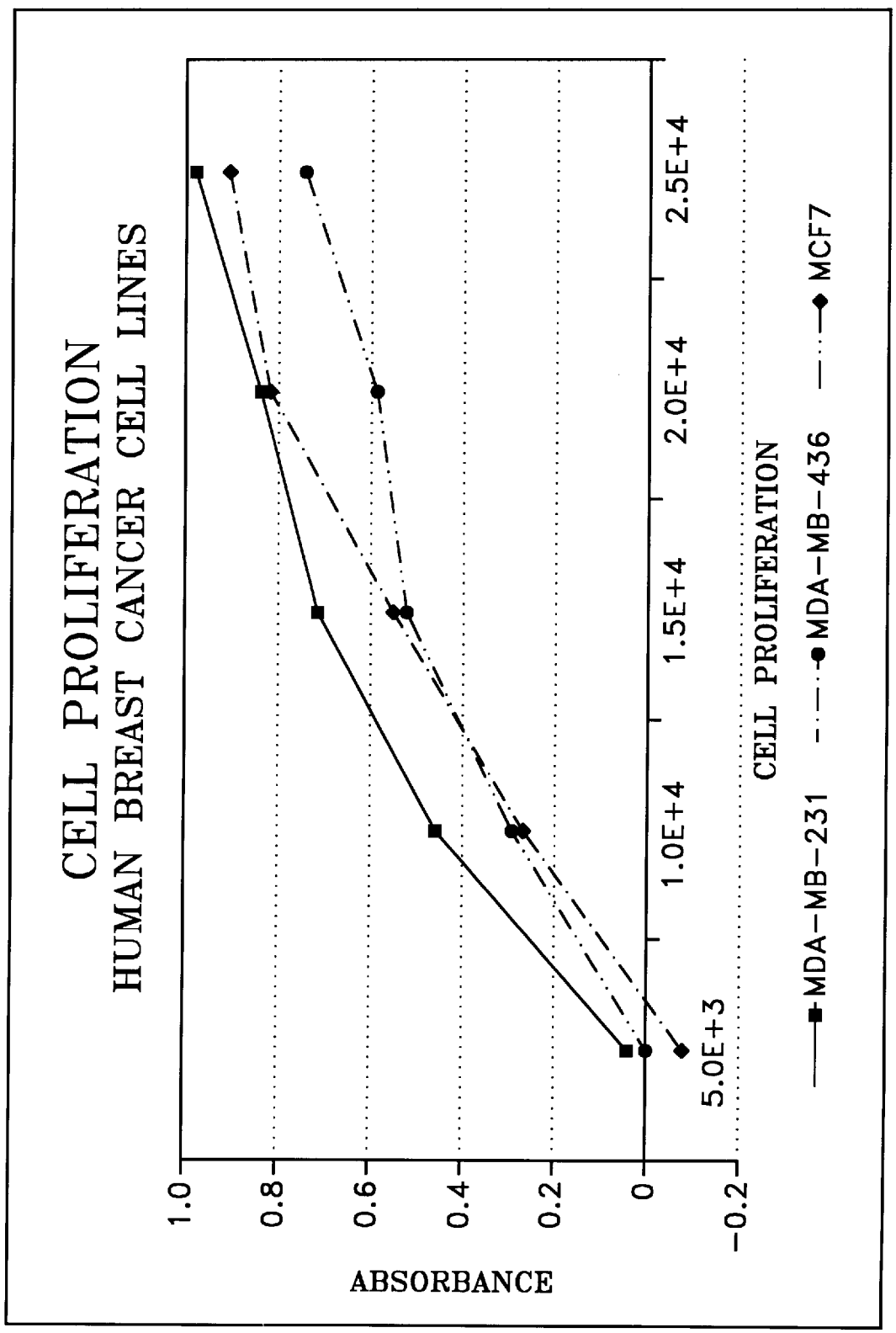
FIG. 1 is a graph showing the cell proliferation of various human breast cancer cell lines.

In FIG. 1, the results of studies involving three types of human breast cancer cells: MDA-MB-231, shown in full lines; MDA-MB-436, shown in dot dash lines; and MCF7, shown in dash dot dot lines, are provided. A first study, represented by FIG. 1, shows cell proliferation as measured by absorbance rates. As the graph shows, each of the three types of human breast cancer cells exhibit similar cell proliferation behavior.

Figure 2:
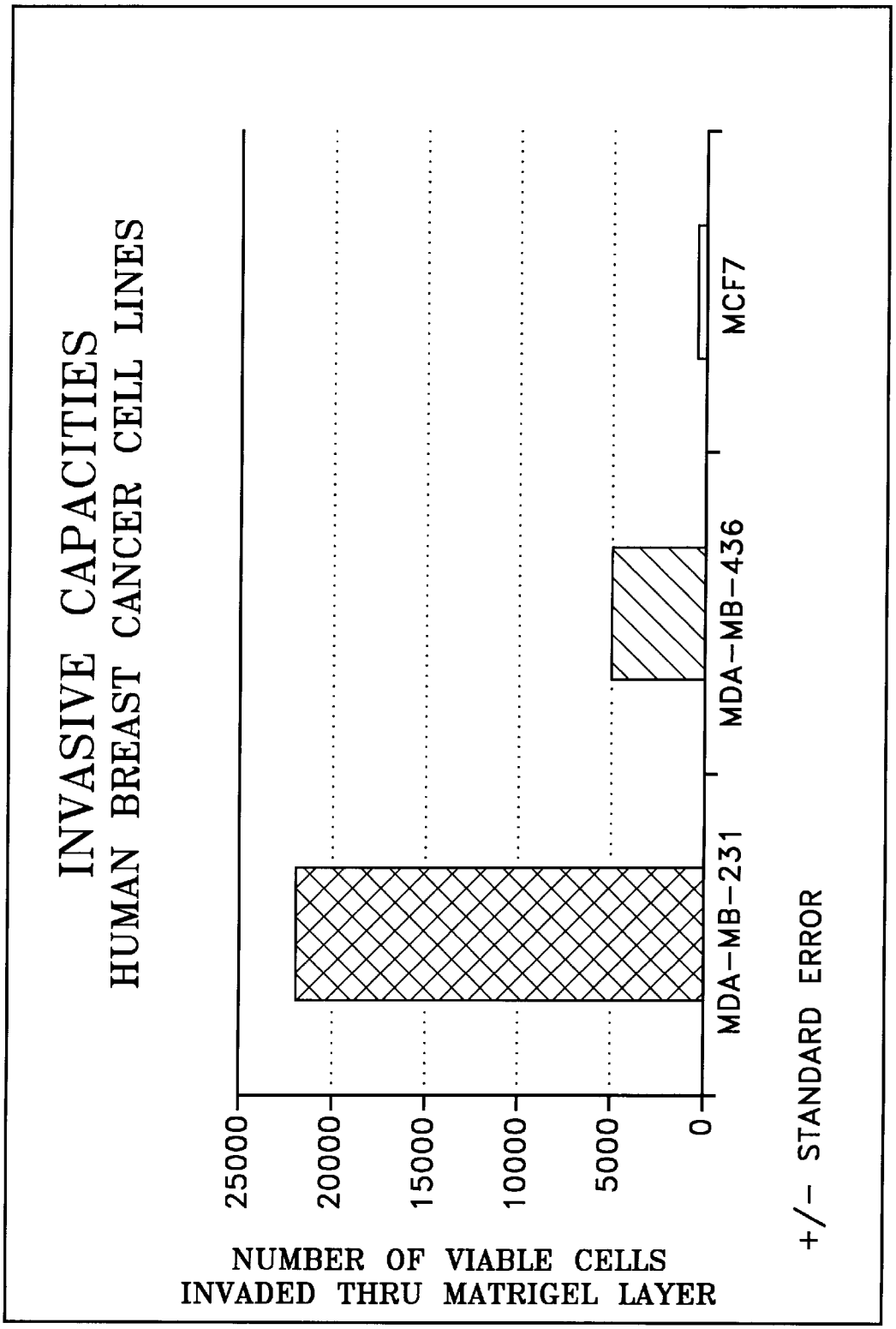
FIG. 2 is a graph showing the invasive capacities of various human breast cancer cell lines.

With respect to FIG. 2, the invasive capacity of the three types of cancer cells was studied using invasion chambers. As is shown, the invasive capacities of the cancer cell lines are very dissimilar. Based on these results, it was concluded that cell proliferation and invasive capacity of human breast cancer cells are separate, non-correlated processes.

Figure 3:
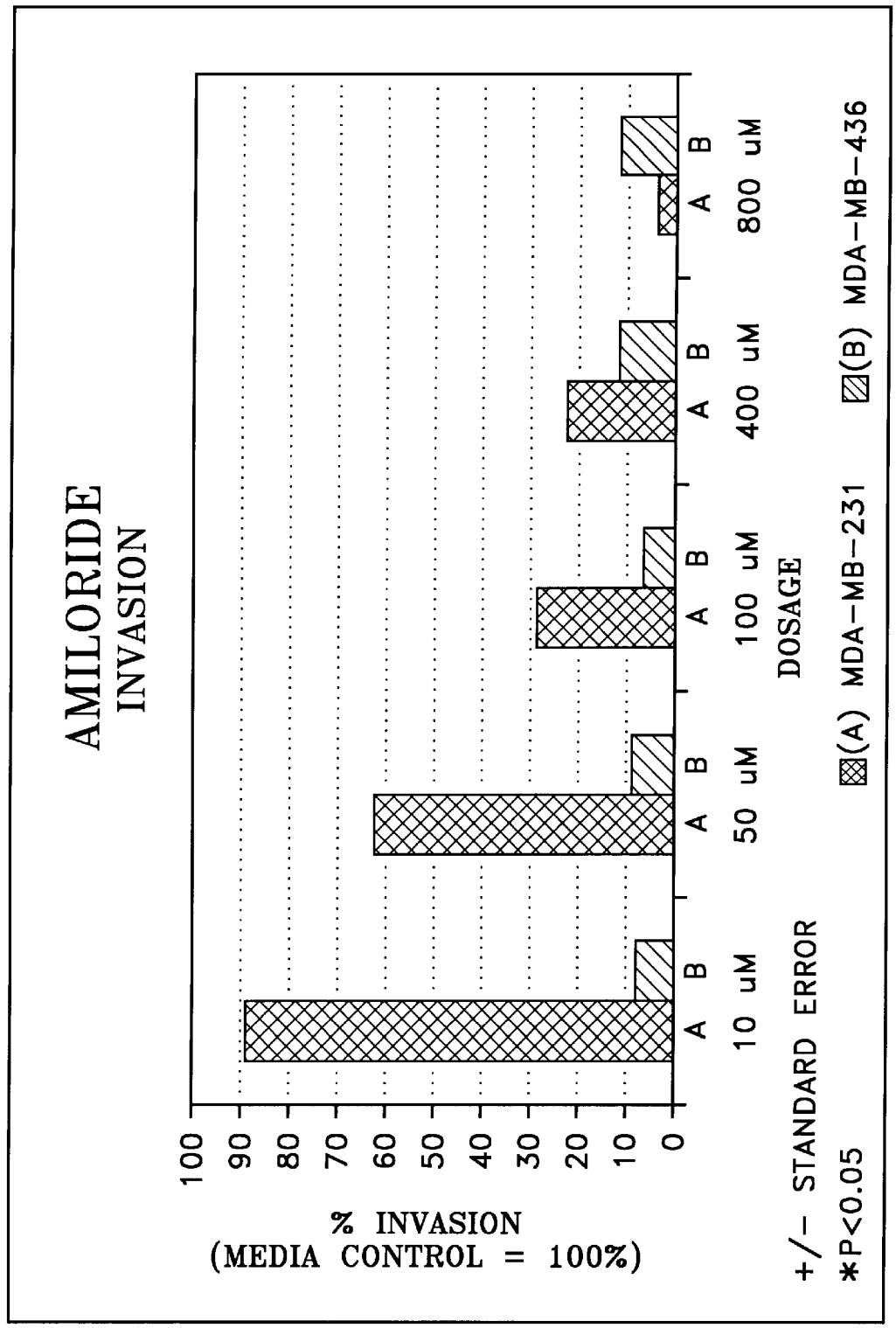
FIG. 3 is a graph showing the effect of amiloride on the invasive properties of various cancer types according to the invention.

In FIG. 3, the effect of amiloride on the invasive capacity of two types of cancer cells, MDA-MB-231 and MDA-MB-436, as compared to respective controls (100%) are shown at dosage levels of from 10 $\mu$M to 800 $\mu$M. Increasing dosage concentrations of amiloride produced obvious effects on the invasion levels measured. Cell viabilities did not vary with the addition of amiloride to the culture medium, even at the highest concentrations.

Figure 4:
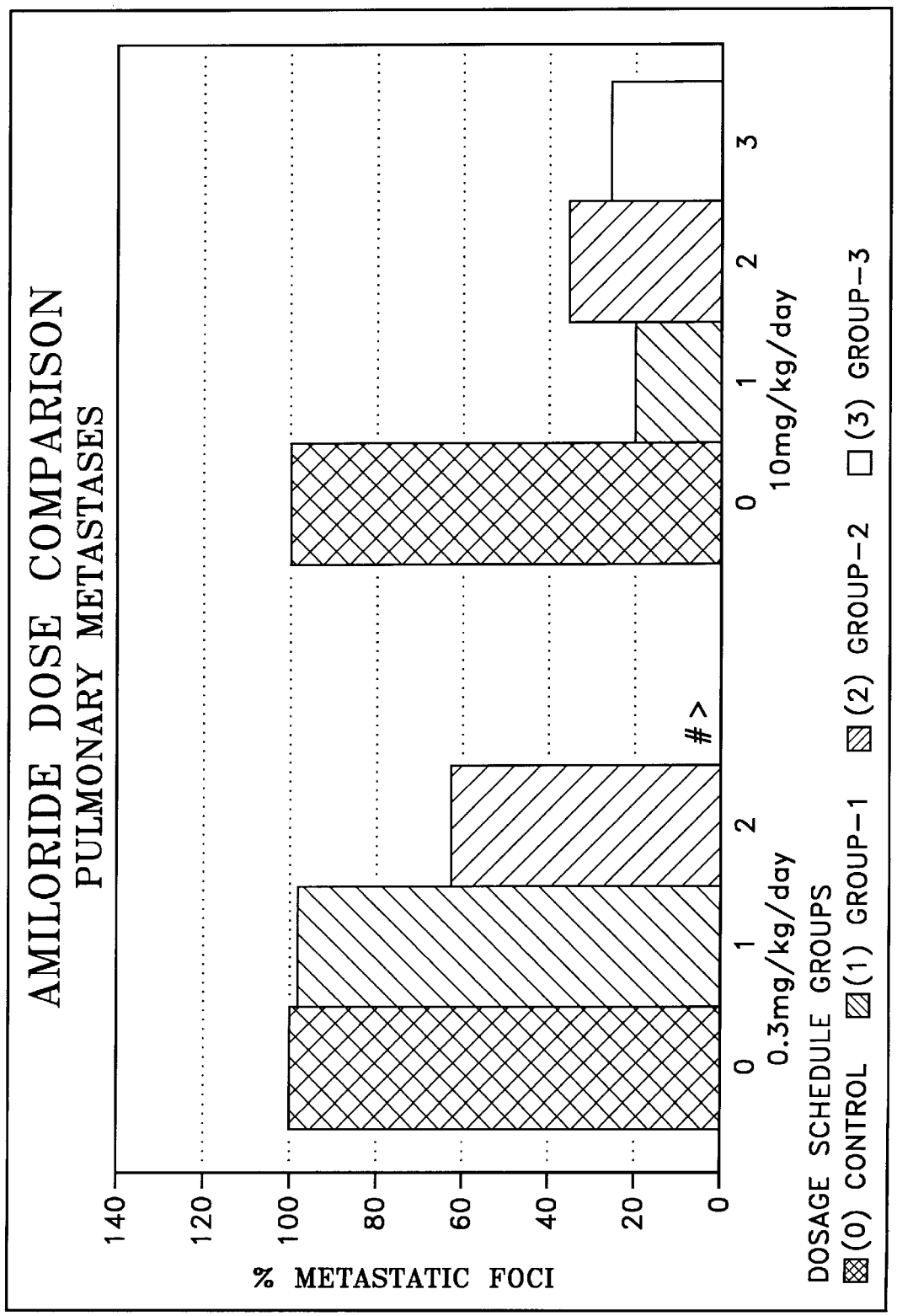
FIG. 4 is a graph showing the changes in metastases of cancer cells due to the action of amiloride according to the invention.

With reference to FIG. 4, a chart showing the effect of the dosage of amiloride on the metastasis of cancer cells in vivo is provided. In this study, MATB 13762 rat mammary cancer cells were maintained in culture with McCoy's 5A (90%) Fetal Bovine Serum (10%) and penicillin-streptomycin 1%. Fresh cultures were brought up from frozen stock and those cells maintained in culture only briefly prior to use in this study. MATB cells were centrifuged and counted for viability with Trypan blue stain on a hemacytometer. Each of the cell populations used for inoculation were found to be 90% viable or better. Two parallel experiments, identical in design but differing in dosage levels, employing 40 Fisher 344 rats each were carried out in the following fashion. Following a two week quarantine and maintenance on standard Purina rat chow and filtered water, each rat was inoculated with a cell suspension of $10^5$ MATB rat mammary cancer cells via direct injection of the jugular venous system. Parallel sets of three groups of ten rats each were administered amiloride initiated in different time sequences and at dosage schedules of 0.3 mg/kg/day and 10 mg/kg/day respectively. All experimental rats received amiloride in drinking water offered in 50 cc graduated cylinders permitting daily measurement of fluid intake. The control group received filtered water containing no amiloride. Group 1 received amiloride commencing on the day of inoculation and continuing to the $10^{th}$ day following inoculation. Group 2 received amiloride beginning 7 days prior to inoculation and continuing to the $10^{th}$ post inoculation day. Group 3 received amiloride beginning at the $7^{th}$ post inoculation day in the low dose study and on the $3^{rd}$ post inoculation day in the high dose study. The studies were concluded at the $10^{th}$ day following the amiloride treatment. The middle lobe of the right lung was harvested from each rat and preserved in formalin. Two sagittal sections from each lobe were prepared for microscopic examination. The numbers of metastatic nodules were counted and recorded. The recorded numbers are expressed as the percentage of controls as shown in FIG. 4.

Each group in both dosage categories showed reduced numbers of metastases as a result of the administration of amiloride, reflecting statistical significance in all groups at the higher dose levels and in Group 2 at the lower dosage. Pulmonary metastases in Group 1 were 21% of control ($p<0.03$) at the high dose of amiloride. The most consistent effect was noted when amiloride was administered both pre- and post-tumor cell inoculation, (Group 2), with 63% ($p<0.05$) and 36% ($p<0.03$) of control in the low and high dose range respectively. The number of metastases was reduced significantly to 26% ($p<0.04$) in Group 3 when amiloride was instituted at the high dose level 3 days following inoculation. However, when low dose amiloride was begun after a 7 day interval, the metastatic involvement had reached confluence of numbers of adjacent metastatic colonies. Consequently a quantitative number of metastases was not obtainable.

The overall results verified that induced metastases can be reduced significantly in the model employed by the administration of amiloride. The degree of inhibition is dependent of the dosage level employed and the timing of amiloride administration.

The Figures show that amiloride does suppress spread of breast cancer cells in Fisher rats and in the invasion chamber studies on human breast cancer cells and that these effects are dose dependent. In addition, a strong correlation has been shown with the level of invasiveness of a given cancer cell type and the level of uPA produced.

Amiloride has been shown to produce significant suppression of the invasion and spread of mammary cancer cells in both the in vivo rat model and in the in vitro testing of human cells. These observations demonstrate a means of significant control of the malignant process when caused by those cancer cell types dependent on the plasminogen/plasmin system for initiation of the invasive cascade.

Further, it has been shown that the mechanisms that permit invasion and spread of cancer cells in the rat are the same as those in man, and that these mechanisms are inhibited on a dose related basis by amiloride.

Amiloride is a drug already in use for the treatment of hypertension in man, and is well tolerated for that purpose. Amiloride, unlike other available means of treating cancer in man, does not depend on a toxic effect on human cells in order to be effective. Rather, amiloride attacks the migratory capability of cells and therefore has no direct toxic effect on normal cells, apart from the manifestations of potassium accumulation. The propensity of amiloride to cause potassium accumulation can be counteracted by the addition of hydrochlorothiazide.

Additional studies by the Applicants attempt to determine whether the addition of hydrochlorothiazide (HCZ) to the administration of amiloride to Fisher rats alters the suppression of pulmonary metastases produced by IV inoculation of MATB cancer cells.

Fisher 344 female rats were inoculated with $10^5$ MATB cells via the internal jugular venous system. Drugs were administered via the drinking water with a daily log of the amount ingested. The experimental design consisted of four groups of ten animals each, 1) filtered water controls, 2) amiloride alone, 3) hydrochlorothiazide alone, 4) combined amiloride and hydrochlorothiazide. Two dosage schedules were employed, 0.3 mg/kg and 3 mg/kg amiloride, 3 and 15 mg/kg hydrochlorothiazide given singly or combined at low and high dosages of amiloride, respectively. In addition, one full set of animals (Group A) received each drug schedule for ten days post inoculation and a second set (Group B) for 17 days post inoculation. At termination, the lungs were harvested and sectioned for microscopic examination. Metastatic implants were counted by two blinded observers and submitted for statistical analysis. Blood was drawn for serum potassium and amiloride levels on days 3, 7, 10, 14 and 17. The results are given below in Table 1.

TABLE 1

| Group A | Control | Amiloride | HCZ | Amiloride/HCZ |
| --- | --- | --- | --- | --- |
| Low | 58.5 | 74.35 [6.3] | 40.5 [3.8]* | 38.31 [4.1]* |
| High | | 71.65 [9.6] | 67.75 [16] | 33.25 [7.0]* |

Mean [standard error], *statistically significant at $P < 0.05$

There was no statistical differences determined for Group B metastases as compared to controls.

At the dosage levels employed in this study there was no significant difference expected in metastases resulting from amiloride alone. Significant suppression of metastases were found by low dose hydrochlorothiazide as compared to controls. Highly significant suppression of metastases resulted from the combination of amiloride and hydrochlorothiazide when administered together. The combination of the primary agent, amiloride, with a secondary agent, such as hydrochlorothiazide, has been shown to produce unexpected results concerning the suppression of metastases. It is believed that other secondary suppressing agents will work in combination with the amiloride to enhance the suppressive effect.

The inhibition of uPA by amiloride has been shown to effectively suppress, but not eliminate, the ability of the cancer cell to invade and spread. Therefore, Applicants have targeted a separate step in the enzymatic cascade through use of a secondary agent. A further study by Applicants focused on the action of amiloride, which is a uPA inhibitor, in combination with batimistat, which is a metalloprotease inhibitor. Again, hydrochlorothiazide, which promotes the excretion of potassium, was studied in combination with the amiloride. The study involved seventy rats in all divided into groups of ten. Each rat was inoculated with intravenous rat breast cancer cells. Ten rats received no inhibitors, ten received amiloride alone, ten received amiloride and hydrochlorothiazide, ten received Batimistat, ten received amiloride and Batimistat in combination, ten received Batimistat and saline and ten received water and saline.

The gross appearance of the animal lungs, which are the target organs for the appearance of tumors, indicates that the combined amiloride and batimistat group had the least detectable level of tumor.

In a further study, three separate cell lines of human breast cancer cells were exposed to amiloride and a synthetic derivative known as B428. The results of this study show clearly that the suppression of invasion of human cancer cells by these inhibitors exceeds that obtained with rat cells in a laboratory invasion chamber.

The invention has been described with reference to preferred embodiment. Obviously, modifications and alterations will occur to others upon a reading and understanding of this specification. It is intended to include all such modifications and alternations in so far as they come within the scope of the appended claims or the equivalence thereof.

Having thus described the invention, it is now claimed:

What is claimed is:

1. A method for treating a host having cancer cells derived from epithelial cells due to an enzymatic cascade triggered by the activation of plasminogen to plasmin by the specific activation of Urokinase Plasminogen Activator (uPA) comprising the steps of:

administering to the host an amount of amiloride sufficient to adversely affect the action of the uPA and thereby suppress invasion and spread of cancer cells in the host; and, administering a secondary agent to the host in combination with the amiloride, the secondary agent being hydrochlorothiazide, wherein the hydrochlorothiazide is provided in an amount effective to provide a synergistic effect on the invasion and spread of cancer cells in combination with the amiloride.

2. The method of claim 1 wherein the amount of amiloride is in the range of 0.3 mg/kg to 3 mg/kg, inclusive.

3. The method of claim 1 wherein the amount of hydrochlorothiazide is in the range of 3 mg/kg to 15 mg/kg, inclusive.

4. A method for treating a host having cancer cells derived from epithelial cells due to an enzymatic cascade triggered by the activation of plasminogen to plasmin by the specific activation of Urokinase Plasminogen Activator (uPA) comprising the steps of:

administering to the host a combination of amiloride in the range of 0.3 mg/kg to 3.0 mg/kg, inclusive, and hydrochlorothiazide in the range of 3 mg/kg to 15 mg/kg, inclusive.

* * * * *